(12) United States Patent
Huang

(10) Patent No.: US 7,564,172 B1
(45) Date of Patent: Jul. 21, 2009

(54) MICRO-ELECTRO-MECHANICAL TRANSDUCER HAVING EMBEDDED SPRINGS

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 0 days.

(21) Appl. No.: 11/462,338

(22) Filed: Aug. 3, 2006

Related U.S. Application Data

(60) Provisional application No. 60/744,242, filed on Apr. 4, 2006, provisional application No. 60/705,606, filed on Aug. 3, 2005.

(51) Int. Cl.
*H01L 41/00* (2006.01)
(52) U.S. Cl. ............... 310/328; 310/346; 310/352; 310/311
(58) Field of Classification Search .......... 310/328, 310/346, 352
See application file for complete search history.

(56) References Cited

U.S. PATENT DOCUMENTS

| | | | | |
|---|---|---|---|---|
| 4,183,126 A | * | 1/1980 | Ikeno et al. | 29/25.35 |
| 5,142,307 A | * | 8/1992 | Elrod et al. | 347/46 |
| 5,597,358 A | * | 1/1997 | Marcu | 472/50 |
| 5,917,272 A | * | 6/1999 | Clark et al. | 310/343 |
| 6,812,055 B2 | * | 11/2004 | Tamura et al. | 438/48 |
| 6,917,086 B2 | * | 7/2005 | Cunningham et al. | 257/415 |
| 2004/0145277 A1 | * | 7/2004 | Horning et al. | 310/328 |

* cited by examiner

*Primary Examiner*—Quyen Leung
*Assistant Examiner*—Bryan P Gordon
(74) *Attorney, Agent, or Firm*—Lee & Hayes, PLLC

(57) ABSTRACT

A micro-electro-mechanical transducer (such as a cMUT) is disclosed. The transducer has a base having a lower portion and an upper portion; a top plate disposed above the upper portion of the base forming a gap therebetween; and a spring-like structure disposed between the top plate and the lower portion of the base. The spring-like structure has a spring layer connected to the lower portion of the base and a spring-plate connector connecting the spring layer and a top plate. In an alternate embodiment, the spring-like has a vertical bendable connector connecting the top plate and the lower portion of the base. The spring-like structure transports the top plate vertically in a piston like manner to perform the function of the transducer. Fabrication methods to make the same are also disclosed.

16 Claims, 10 Drawing Sheets

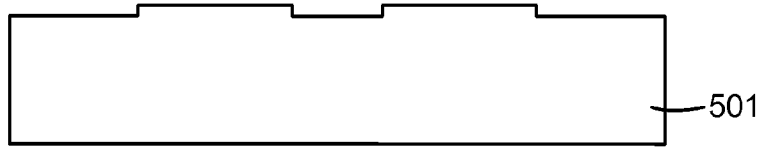
FIG. 5.1
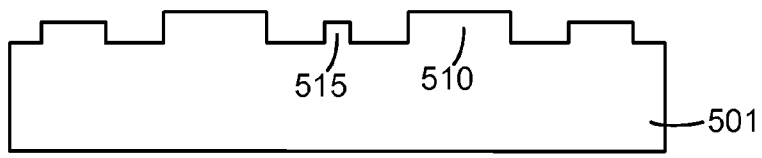
FIG. 5.2
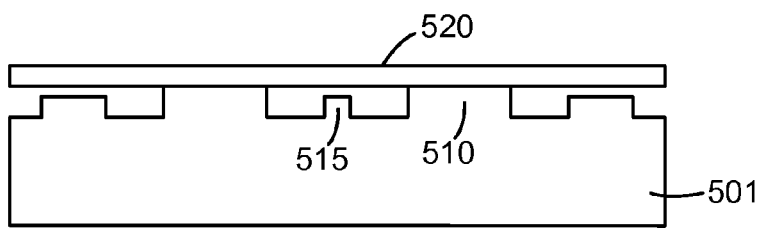
FIG. 5.3
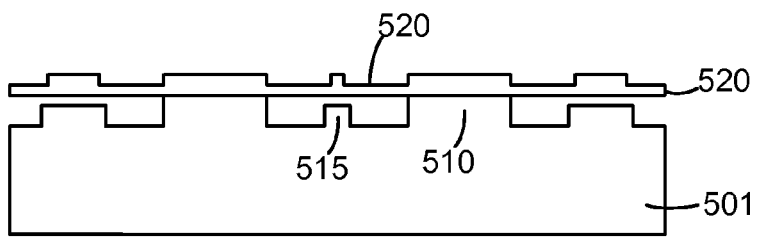
FIG. 5.4

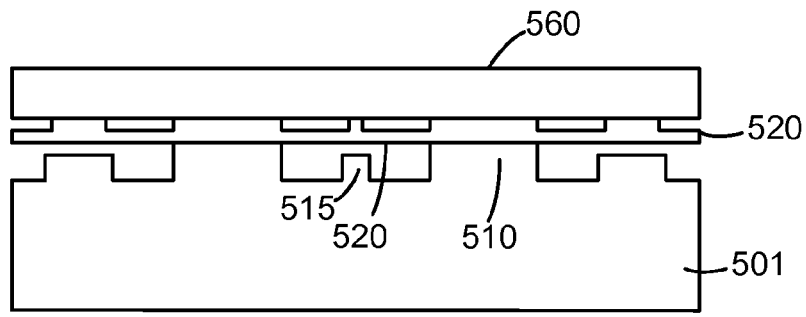
FIG. 5.5
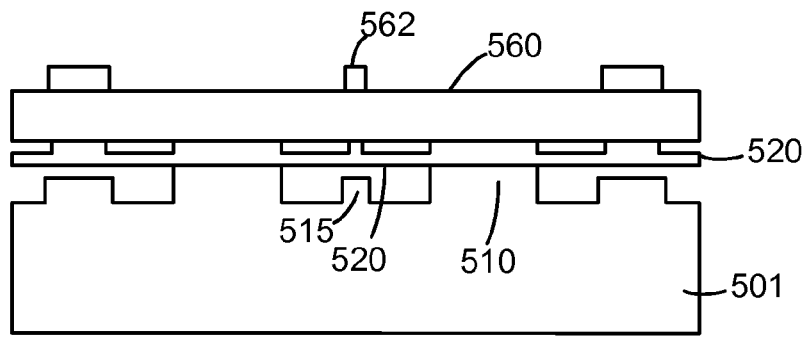
FIG. 5.6
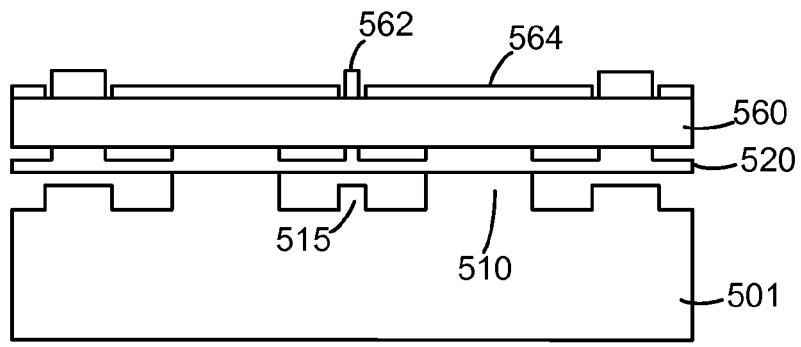
FIG. 5.7
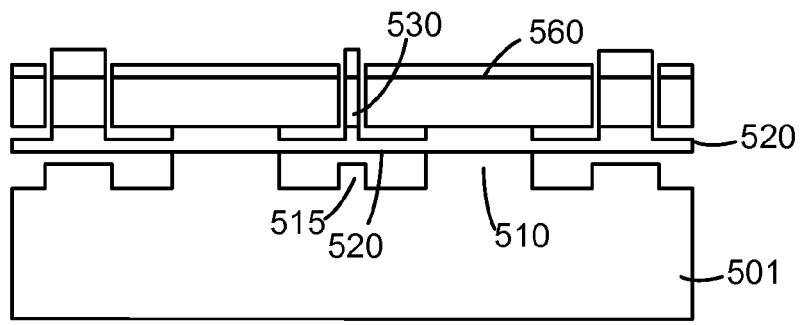
FIG. 5.8

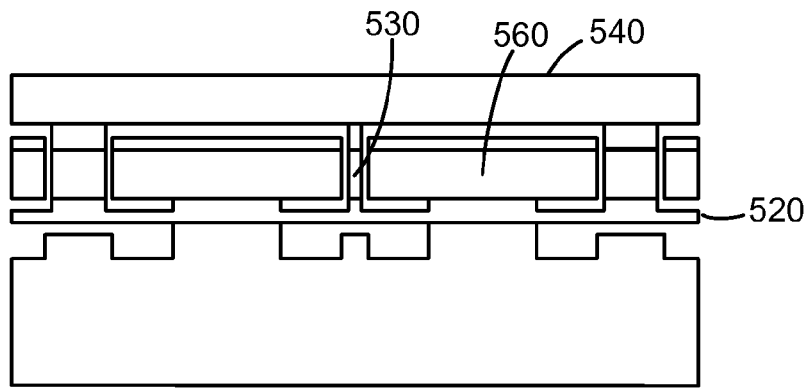
FIG. 5.9
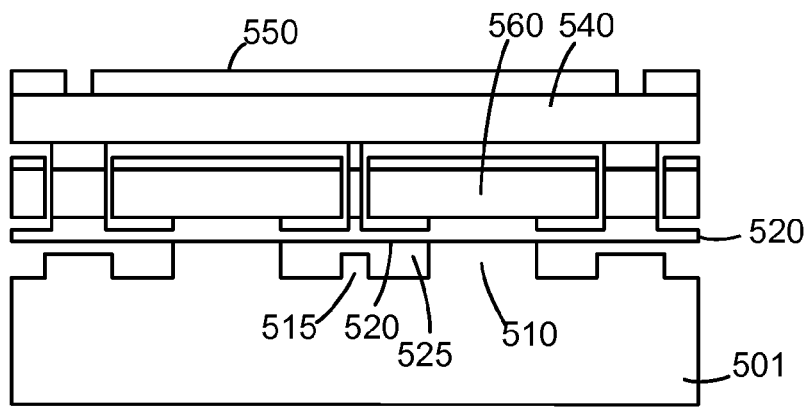
FIG. 5.10
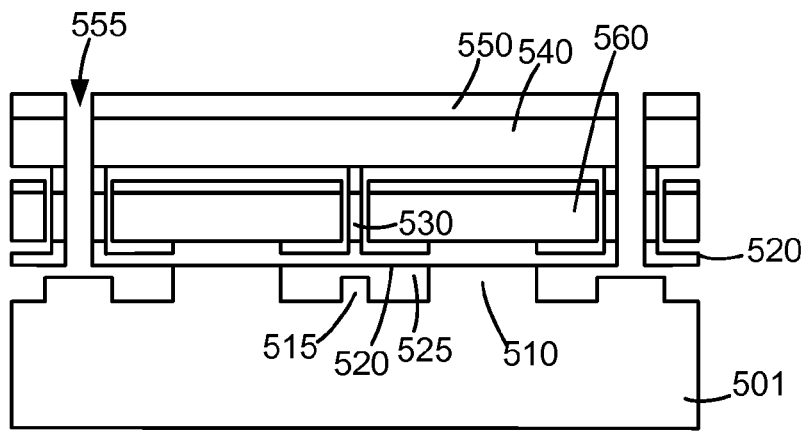
FIG. 5.11

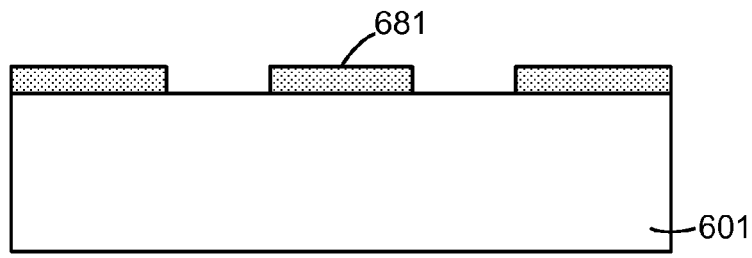
FIG. 6.1
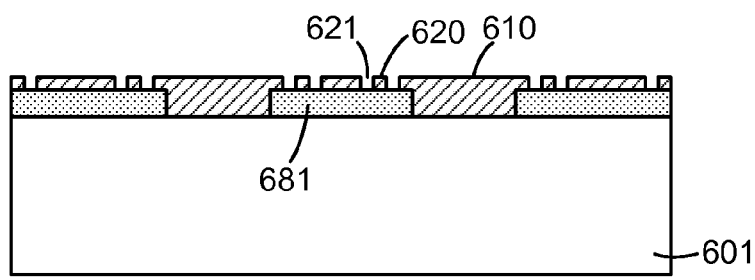
FIG. 6.2
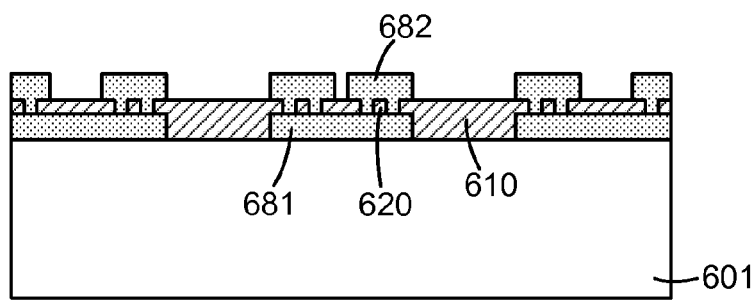
FIG. 6.3
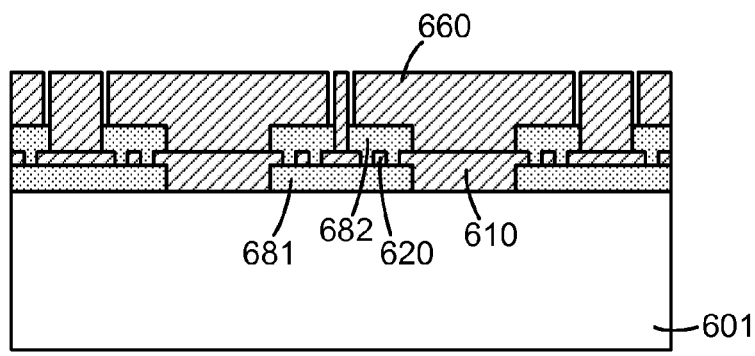
FIG. 6.4

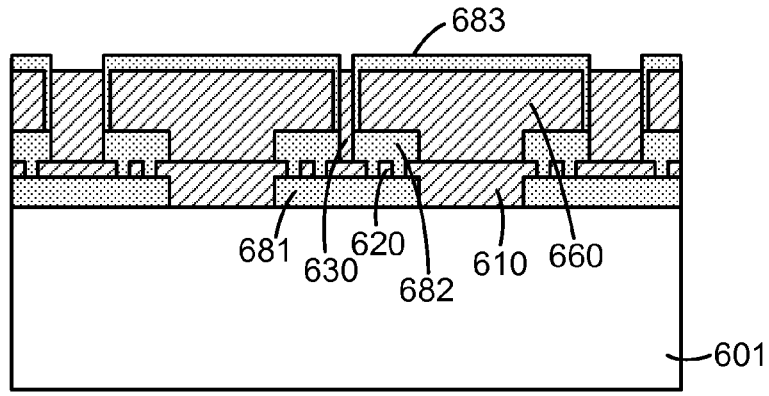
FIG. 6.5
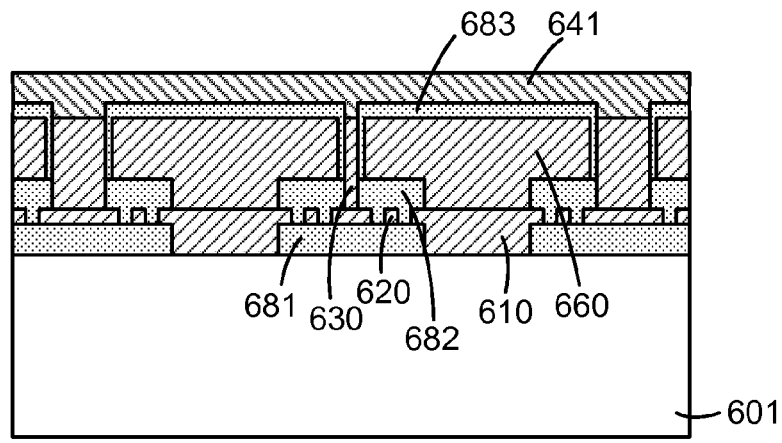
FIG. 6.6
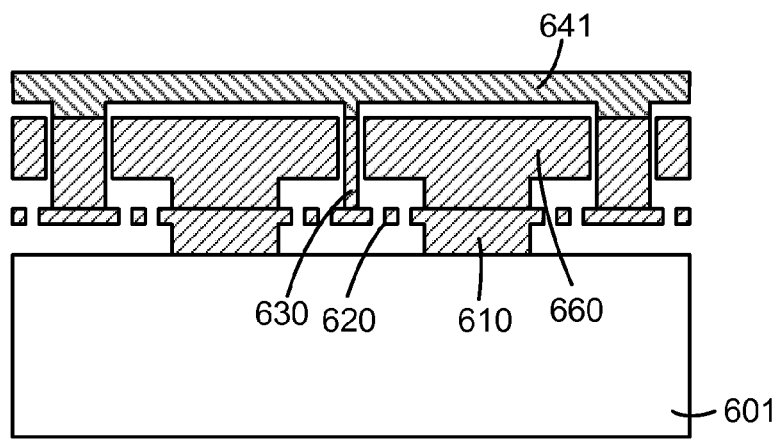
FIG. 6.7

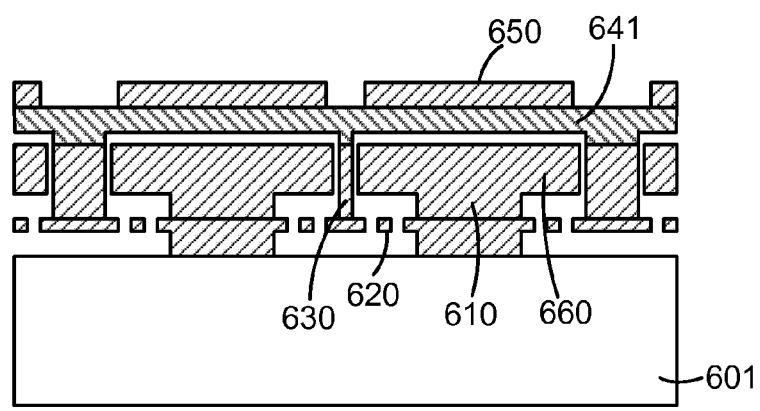
FIG. 6.8
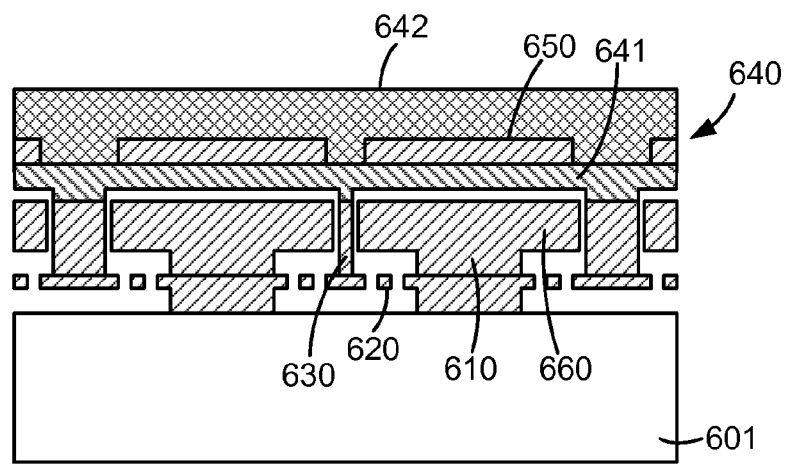
FIG. 6.9
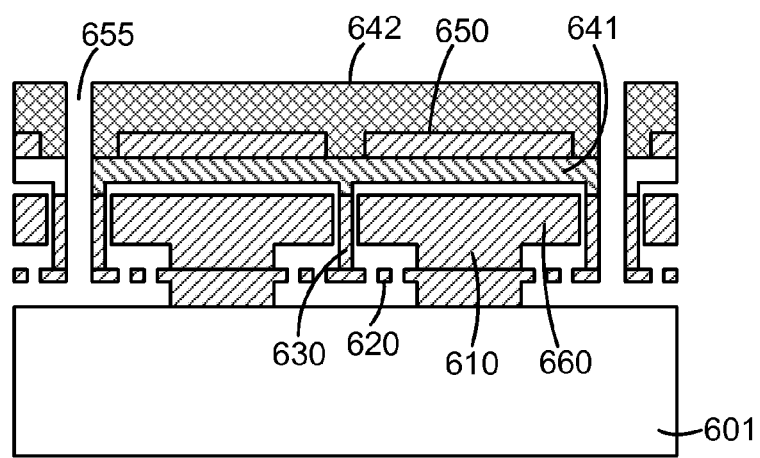
FIG. 6.10

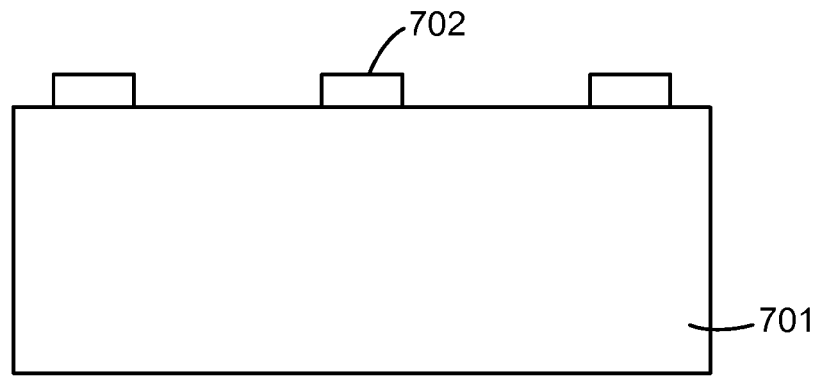
FIG. 7.1
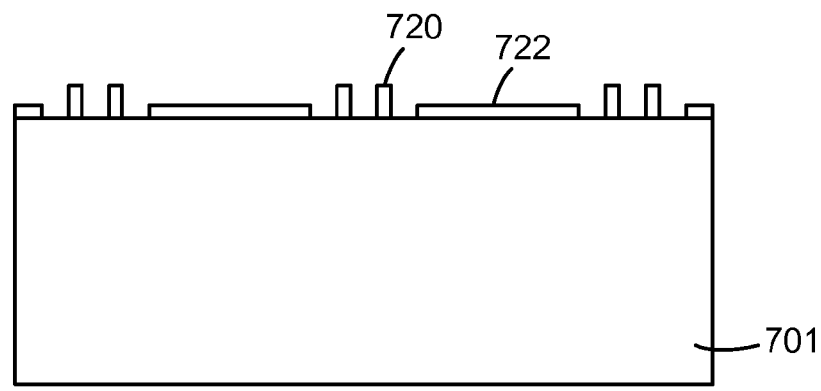
FIG. 7.2
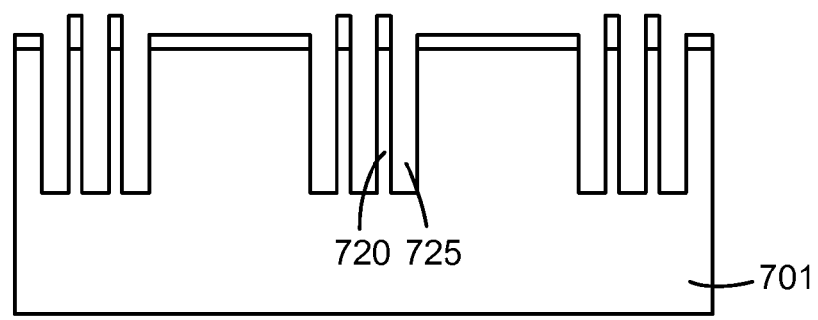
FIG. 7.3

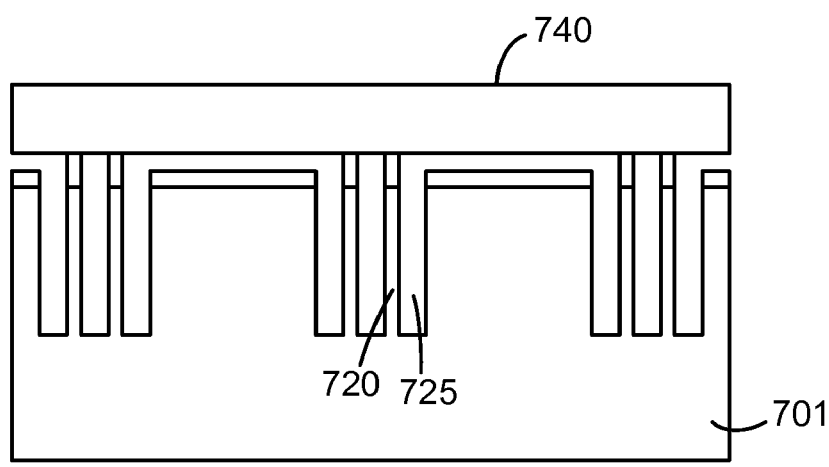
FIG. 7.4
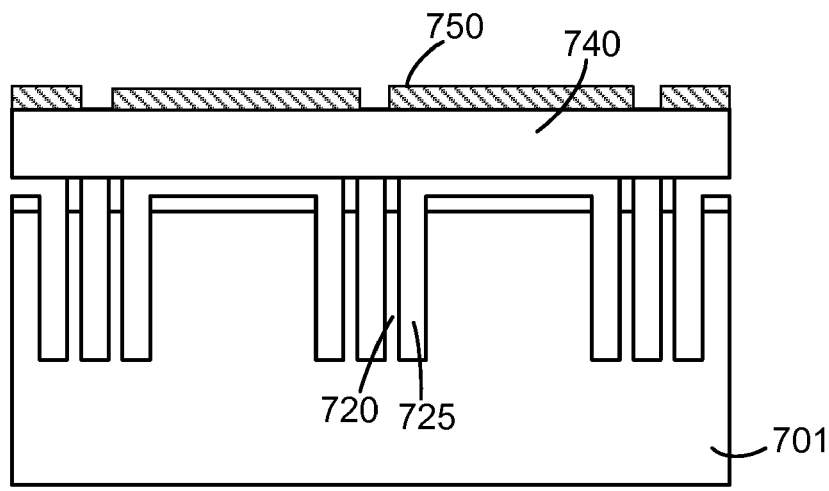
FIG. 7.5
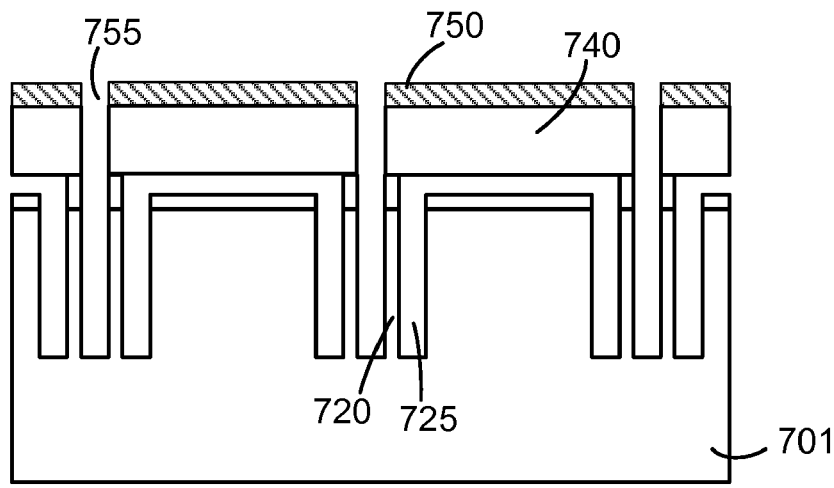
FIG. 7.6

MICRO-ELECTRO-MECHANICAL TRANSDUCER HAVING EMBEDDED SPRINGS

PRIORITY

This application claims priority from U.S. Provisional Application Ser. No. 60/705,606, filed Aug. 3, 2005, and Ser. No. 60/744,242, filed Apr. 4, 2006, which applications are incorporated herein by reference in their entirety.

This application further incorporates herein by reference in entirety the following:

International Application (PCT) No. PCT/IB2006/051567, entitled METHODS FOR FABRICATING MICRO-ELECTRO-MECHANICAL DEVICES, filed on May 18, 2006;

International Application (PCT) No. PCT/IB2006/051568, entitled MICRO-ELECTRO-MECHANICAL TRANSDUCERS, filed on May 18, 2006;

International Application (PCT) No. PCT/IB2006/051569, entitled MICRO-ELECTRO-MECHANICAL TRANSDUCERS, filed on May 18, 2006; and International Application (PCT) No. PCT/IB2006/051948, entitled MICRO-ELECTRO-MECHANICAL TRANSDUCER HAVING AN INSULATION EXTENSION, filed on Jun. 16, 2006.

FIELD OF THE INVENTION

The present invention relates to micro-electro-mechanical devices that have a movable mechanical part for energy transformation, particularly to micromachined ultrasonic transducers (MUT) such as capacitive micromachined ultrasonic transducers (cMUT).

BACKGROUND OF THE INVENTION

Micro-electro-mechanical transducers usually share a common feature which includes a movable mechanical part used for energy transformation. One example of such micro-electro-mechanical transducers is micromachined ultrasonic transducers (MUT). An ultrasound transducer performs a chain of energy transformation to realize its function of a transducer. In its receiving mode, the acoustic energy of ultrasound waves propagating in a medium where the transducer is placed is transformed to mechanical energy of a movable part (conventionally a vibrating membrane) in the transducer. The motion of the movable part is then transformed to a detectable electromagnetic (usually electrical) signal. In its transmitter mode, the reverse chain of energy transformation takes place.

Various types of ultrasonic transducers have been developed for transmitting and receiving ultrasound waves. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

Among the several types of MUTs, the capacitive micromachined ultrasonic transducer (cMUT), which uses electrostatic transducers, is widely used. FIG. 1 shows a cross-sectional view of a basic structure of a prior art cMUT. The cMUT 10 of FIG. 1 is built on a substrate 11. Each cMUT cell has a parallel plate capacitor consisting of a rigid bottom electrode 12 and a top electrode 14 residing on or within a flexible membrane 16 that is used to transmit or receive an acoustic wave in the adjacent medium. The flexible membrane 16 in each cell is supported by the anchor 18. The membrane 16 is spaced from the substrate 11 and the top electrode 12 to define a transducing space 19 therebetween. A DC bias voltage is applied between the electrodes 12 and 14 to deflect the membrane 16 to an optimal position for cMUT operation, usually with the goal of maximizing sensitivity and bandwidth. During transmission an AC signal is applied to the transducer. The alternating electrostatic force between the top electrode and the bottom electrode actuates the membrane 16 in order to deliver acoustic energy into the medium (not shown) surrounding the cMUT 10. During reception the impinging acoustic wave vibrates the membrane 16, thus altering the capacitance between the two electrodes. An electronic circuit detects this capacitance change.

There are drawbacks in the cMUTs of the prior art structures and methods. Many of these drawbacks relate to the fact that each addressable cMUT element is made of many individual cells and each cell has its cMUT membrane clamped or fixed on edges shared by the adjacent cells. Specifically, there exists a cell limitation in the design of the cMUT showing in FIG. 1. For example, the required acoustic performance limits the overall size of each single cMUT cell 10. A large cMUT cell would require a large membrane 16, which would have to be very rigid and thick in order to maintain the required resonant frequency. Because of this important limitation of the conventional cMUT structure, each addressable cMUT element of the prior art must be made of multi-cells. For example, in a cMUT structure used in medical phase array, the cMUT element size is the half wavelength of the acoustic wave (e.g., 75 um for a 10 MHz device, 150 um for a 5 MHz device and 750 um for a 1 MHz device). In order to achieve the required device operation frequency, the size of the conventional cMUT cells must be made much smaller than the element or device size without having to use an unreasonably thick membrane.

Examples of the drawbacks of the prior art cMUT's are listed below.

(1) The average displacement of the membranes is small because of the clamped edges. As a result both the device transmission and reception performance are poor.

(2) Surface areas occupied by the clamped areas (e.g., edges) and the walls or posts are non-active, thus reducing the device fill factor and the overall efficiency.

(3) Anchor areas introduce a parasitic capacitance which decreases the device sensitivity.

(4) The anchor pattern within the surface of the cMUT element may cause ultrasonic wave interference which limits the device bandwidth.

(5) The non-uniform displacement of the membrane may disturb the ultrasonic wave pattern. For example, the non-uniform displacement may affect the ultrasonic beam pattern emitted from the transducer surface and also cause acoustic cross coupling through the transducer surface.

(6) The resonant frequencies of individual cells in the same cMUT element may be different between each other because of the process variation. This causes phase differences of the membrane motion among different cells in the same cMUT element during operation. As a result, the sum of the average displacement of the cMUT element may degrade dramatically. This problem degrades the device performance especially when the cMUT works in a high quality factor (Q-factor) condition, for example in air.

(7) The acoustic energy can couple into the transducer substrate through supporting walls and cause undesired effects such as acoustic cross coupling between the cMUT elements. An effort to reduce the cross-coupling through the substrate by introducing materials with desired acoustic properties may require occupation of extra space between elements.

In addition, the equivalent mass and spring constant of the cMUT shown in FIG. 1 are highly dependent on each other. It is hard or almost impossible to change one without also changing the other. This negatively affects the device design flexibility.

Due to the importance of these MUT devices, it is desirable to improve the technology in terms of performance, functionality, and manufacturability.

SUMMARY OF THE INVENTION

This patent application discloses a micro-electro-mechanical transducer (such as a cMUT) having a spring-like structure and methods for making the same. The transducer has a base having a lower portion and an upper portion; a top plate disposed above the upper portion of the base forming a gap therebetween; and a spring-like structure disposed between the top plate and the lower portion of the base.

The spring-like structure has a spring layer connected to the lower portion of the base and a spring-plate connector connecting the spring layer and a top plate. According to one embodiment, the lower portion has a sidewall receding from an edge of the upper portion to define a cavity under the upper portion, and the spring layer is connected to the sidewall of the lower portion to form a cantilever disposed in the cavity. A motion stopper may be placed under the spring layer to limit a maximum vertical displacement thereof.

In an alternative embodiment, the spring-like has a vertical bendable connector connecting the top plate and the lower portion of the base. The spring-like structure transports the top plate vertically in a piston like manner to perform the function of the transducer. In one embodiment, the upper portion of the base comprises a layer material having a pattern of trench openings passing from a top to the lower portion of the base, wherein the spring-like structure comprises a plurality of vertical bendable connectors disposed in the pattern of trench openings.

The micro-electro-mechanical transducer may be an electrostatic transducer which has an electrode as its transducing member. In addition to a first electrode on the top plate, the upper portion of the base may also include or carry an electrode. For example, the upper portion of the base may be a conductive layer serving as an electrode. Alternatively, a separate conductive layer may be disposed on the upper portion to serve as an electrode.

According to another aspect of the present invention, a micro-electro-mechanical transducer comprises a first support layer supporting a first electrode; a second support layer supporting a second electrode, the second support layer having a pattern of openings and being connected to a substrate through a plurality of anchors; a spring layer below the second support layer, the spring layer being connected to the plurality of anchors at various locations; and a plurality of vertical connectors each passing through the pattern of openings on the second support layer to connect the first support layer and the spring layer.

In one embodiment, the plurality of anchors each have a sidewall receding from an edge of a nearby opening of the second support layer to define a cavity under the second support layer, and wherein the spring layer forms a plurality of cantilevers each anchored at the respective sidewall of the plurality of anchors.

In one embodiment, the vertical bendable connector has a curved shape. In other embodiment, the vertical bendable connector connects to the lower portion of the base through an anchor layer.

The foregoing and other features and advantages will become more apparent from the following detailed description of several embodiments, which proceeds with reference to the accompanying figures.

BRIEF DESCRIPTION OF THE DRAWINGS

FIGS. 5.1-5.11 show a fabrication process for making a cMUT of the present invention using wafer bonding process.

FIGS. 6.1-6.10 show a fabrication process for making a cMUT of the present invention using sacrificial technology.

FIGS. 7.1-7.7 show a fabrication process for making another cMUT of the present invention.

DETAILED DESCRIPTION

Figure 1:
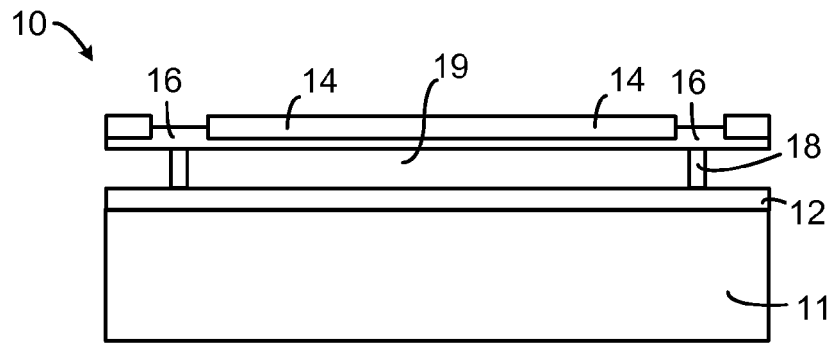
FIG. 1 shows a cross-sectional view of a basic structure of a prior art cMUT.

The micro-electro-mechanical transducer such as a capacitive micromachined ultrasonic transducer (cMUT) of the present invention will be described in detail along with the figures, in which like parts are denoted with like reference numerals or letters. Fabrication methods for making the micro-electro-mechanical transducer of the present invention are also disclosed. These methods may be used in combination with any suitable methods, particularly using the methods disclosed in the several patent applications identified herein.

The invention has been described below with reference to specific embodiments. In most cases, a cMUT structure is used to illustrate the invention. It is appreciated, however, that the present invention is not limited to cMUTs. It will be apparent to those skilled in the art that various modifications may be made and other embodiments can be used without departing from the broader scope of the inventions. Therefore, these and other variations upon the specific embodiments are intended to be covered by the present inventions.

Those skilled in the art will recognize that various features disclosed in connection with the embodiments may be used either individually or jointly.

In this document, a conductive material is defined as one having a resistivity less than $1 \times 10^4$ Ω-cm. Silicon and polysilicon materials are therefore considered conductive materials in this context. A good conductive material preferably has a resistivity less than 1 Ω-cm. The terms "insulation material", "insulating material" and "dielectric material" are used interchangeably unless noted otherwise, and are defined as one having a resistivity greater than $1 \times 10^4$ Ω-cm. A good insulation/insulating material preferably has a resistivity greater than $1 \times 10^8$ Ω-cm. An insulator generally comprises an insulating material but in special cases may include air and vacuum.

It is noted that the terms "transducer" and "transducing member" are used in a broad sense in this document to not only include devices that perform both actuation and sensing functions but also include devices that perform either an actuation function or an sensing function. It is also noted that the term "cantilever" is used in this description in a broad sense to describe a structure that has an anchored end, a resilient portion extending from the anchored, and to an exerting end to activate or move the resilient portion. A cantilever thus does not necessarily suggest a literal one-dimensional beam-like cantilever, but also includes similar structures have multibeams extending in different directions such as a bridge, or a crossbar, and most definitely also includes area or plane springs (two-dimensional "cantilevers") in which the anchored end is an extended line which may be a closed perimeter of an area or a portion thereof, the resilient portion is an extended area, and the exerting end may be a single point, a small area, or an extended line (close ended, open-ended, or segmented). In addition, the words "circular" and "annular" only suggest in the broadest sense that a shape has a looped form, a curved shape that is nearly looped, or an arrangement that is generally shaped like a ring, and do not suggest a rounded shape or any other shape in particular, nor does it suggest that the loop or ring is entirely complete or unbroken.

The present invention is in furtherance or supplement to the novel designs of micromachined transducers such as MUTs invented by the common inventor, as disclosed in the several patent applications referenced to and incorporated herein. The MUTs having embedded springs take a significant departure from the conventional MUT designs. Not only are the basic building blocks (units) of the MUT structure different from that have the conventional structures, but also the new designs are free from the conventional cMUT cell boundary requirement. The present invention follows the same general scheme of the MUTs having embedded springs, but with several additional novel designs of the embedded spring structures.

As will be shown next, although the present invention may still be used to fabricate cMUT elements each having multiple cells, it is not limited to such applications or requirements. In fact, due to the inherent characteristics of the cMUT design in accordance with the present invention, it may be preferable from a fabrication point of view to make each addressable cMUT element without any internal cell boundaries. In addition, even when an addressable cMUT element in accordance with the present invention is made of multiple smaller segments (such as areas each having its own top plate layer segment and spring layer segment separated from that of others), these smaller segments do not need to have a clamped perimeter or a peripheral support wall, and further do not need to be identical to each other in size or shape.

Figure 2:
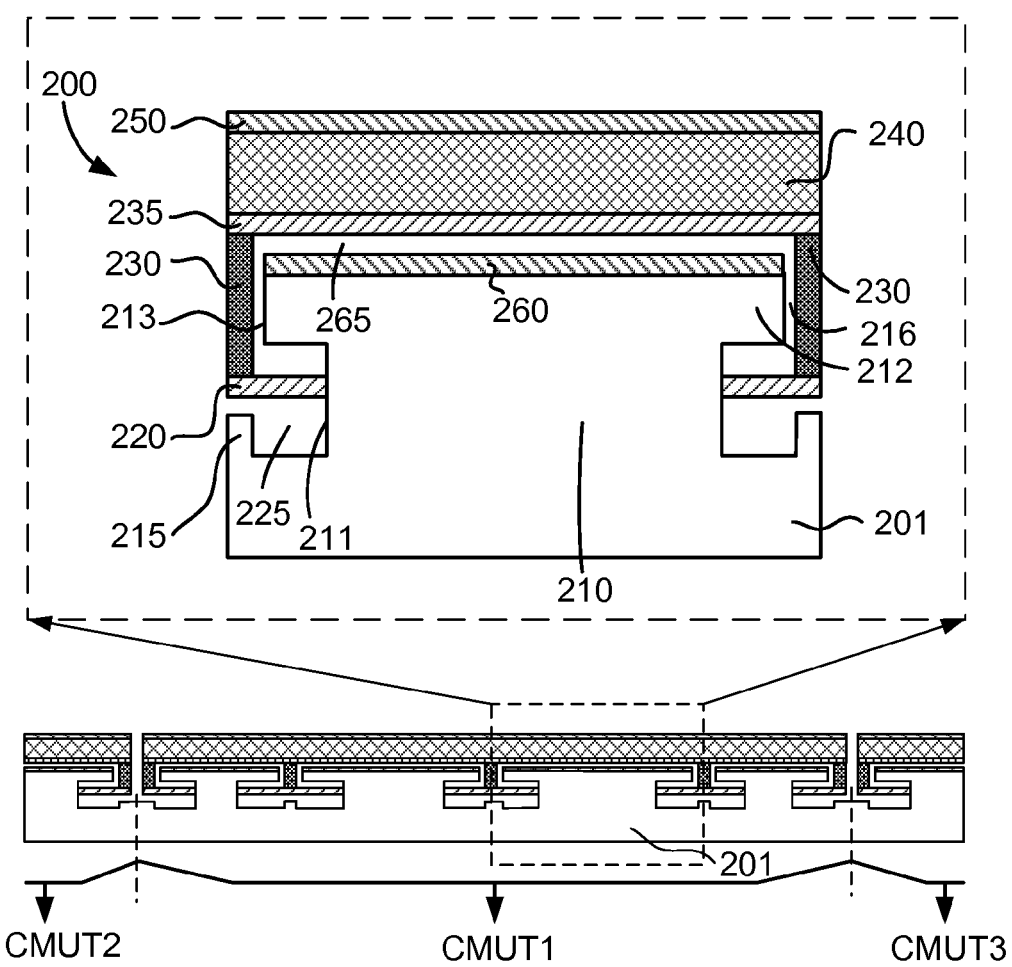
FIG. 2 shows a first embodiment of an embedded-spring cMUT in accordance with the present invention.

FIG. 2 shows a first embodiment of an embedded-spring cMUT in accordance with the present invention. An enlarged view of a selected portion 200 of an embedded spring micro-electro-mechanical transducer (ESMUT) is placed within a rectangle of dashed lines. The ESMUT portion 200 is a part of a complete ESMUT element CMUT1 which may be a separate device alone or a part of a complete cMUT device having multiple cMUT elements (CMUT1, CMUT2 and CMUT3 as shown).

An ESCMUT unit is shown in the selected portion 200 in order to give structural context. The structure of the selected ESMUT portion 200 provides a basis to understand the complete ESMUT element as described in the several PCT patent applications referenced herein.

For certain application such as an ESMUT with a high operation frequency, a full ESMUT element or device may use only one basic unit of the ESMUT portion 200. For other applications, it may be preferred to use a combination of multiple basic units shown in FIG. 2, or any mixed combination of the basic unit shown in FIG. 2 with other basic ESMUT units described hearing or in the several patent applications referenced to and incorporated herein.

The ESMUT portion 200 is built on a substrate 201, on which is a base including a lower base portion 210 and an upper base portion 212. A top plate 240 is disposed above the upper base portion 212 forming a gap 265 therebetween. A spring-like structure having a spring layer 220 and a spring-plate connector 230 is disposed between the top plate 240 and the lower base portion 210. The spring layer 220 is connected to the lower base portion 210 to form a cantilever-like spring. This spring-plate connector 230 connects the spring layer 220 and the top plate 240. In operation, bending of the spring layer 220 causes a vertical displacement of the spring-plate connector 230, which in turn vertically transport the top plate 240. As the top plate 240 is connected by multiple spring-plate connectors 230 similar to each other, bending of the spring layer 220 results in a vertical translation movement by the top plate 240. In some embodiments, the top plate 240 is desirably a rigid plate (being significantly more rigid than the spring layer 220), and thus can be transported in a piston like fashion.

To avoid electric shorting, the top plate 240 also includes an optional insulation layer 235 placed at the bottom in direct contact with the spring-played connectors 230. If the top plate 240 is made of an insulating material providing sufficient insulation, a separate insulation layer is not needed.

In the particular embodiment shown in FIG. 2, motion stoppers 215 are also formed on the bottom surface of the cavity 225. The motion stoppers 215 are placed below the spring layer 220 to limit its maximum vertical displacement, which in turn limits the maximum vertical displacement (transportation distance) of the top plate 240 may experience. If the maximum vertical displacement of the top plate 240 is limited to be smaller than the gap 265, electric shorting between the two electrodes 250 and 260 may be effectively avoided. Proper use of motion stoppers 215 thus enhances reliability of the cMUT. In addition, the need for an insulation layer such as 235 may be eliminated in a design having motion stoppers. Alternatively, motion stoppers may also be placed in the gap defined between the top plate 240 (including the insulation layer 235 in the embodiment shown) and the upper portion 212 (including a top electrode 260 in the embodiment shown) of the base to obtain a similar motion stopping function. In this alternative, motion stoppers may either be placed on the bottom surface of the insulation layer 235 or the top surface of the bottom electrode 260. The motion stoppers may also include an insulation extension extending into the layer to which it is connected. Examples of such insulation extension are described in International Application (PCT) No. PCT/IB2006/051948, entitled MICRO-ELECTRO-MECHANICAL TRANSDUCER HAVING AN INSULATION EXTENSION, filed on Jun. 16, 2006, which application is incorporated by reference herein.

In the particular embodiment shown in FIG. 2, the lower portion 210 has a sidewall 211 receding from an edge 213 of the upper portion 212 to define a cavity 225 under the upper portion 212. The spring layer 220 is connected to the sidewall 211 of the lower portion 210 to form a cantilever under the upper portion 212 of the base. The cantilever is generally disposed in the cavity 225. In a cMUT configuration, the top plate 240 further has a top electrode 250 as one of its transducer members. Correspondingly, the top of the upper portion 212 of the base has a bottom electrode 260, which may either be a separate layer disposed on rest of the upper portion 212, or an integral part of the upper portion 212 if the upper portion 212 is made of a conductive material.

Although the cross-sectional view in FIG. 2 shows the cantilever formed by the spring layer 220 to be single-beam like, in some preferred embodiments the cantilever is in a plane formation to form a two dimensional "beam". A functional addressable cMUT element, for example, may include a plurality of the basic units as illustrated above. When viewed as a whole, the cMUT element (including the cMUT portion 200 shown) may be seen as having a three main layers including (1) a first support layer (the top plate 240) supporting a first electrode (the top electrode 250); a second support layer (the upper portion 212 of the base) supporting a second electrode 260; and a spring layer 220 disposed below the second support layer (the upper portion 212 of the base). The second support layer (the upper portion 212 of the base) has a pattern of openings 216 and is connected to substrate 201 through a plurality of anchors (the lower portion 210 of the base). The pattern of openings 216 may include either discrete (separate) narrow openings or extended openings extending across the surface area of the upper portion 212. Anchors (210) have sidewalls 211 to which the spring layer 220 is connected at various locations. Various patterns of openings 216 may be used to configure various distribution profiles of the springs (cantilever-like springs in the embodiment shown in FIG. 2) of the present invention across the cMUT area to obtain the desired acoustic characteristics of the transducer. The distribution profile of the springs may be adjusted with respect to several factors, including the spring strengths of individual springs and locations of that each individual springs.

The cMUT element further has a plurality of vertical connectors 230 passing through the pattern of openings 216 on the second support layer (the upper portion 212) at various locations to connect the first support layer (the top plate 240) and the spring layer 220. For each addressable cMUT element, the top plate 240 may be a continuous plate member moving as a single piece, although as described in the several patent applications referenced to and incorporated herein the top plate 240 may have engineered structures such as hollows and holes to enhance the rigidity/mass ratio. The top plate 240 of each addressable cMUT element is thus supported and transported by a plurality of cantilever-like springs which can be freely distributed across the entire cMUT element area depending on the performance requirement.

In some embodiments, the spring layer 220 is a continuous layer disposed over cavities 225 and under the upper portion 212 of the base. The spring layer 220 thus occupies the entire device element area longitudinally (i.e., in the lateral or surface dimension). This configuration allows the entire top plate 240 to be supported by cantilevers through connectors 230 that can be placed or distributed across the entire device element area without being limited to places near the edge of the element. It is appreciated, however, that the spring layer 220 may comprise multiple small segments that are either connected to each other at certain points or completely separated from each other.

With this design, a cMUT element with a very large active area may be formed. The operating frequency or frequency response of the cMUT element may be adjusted not only by selection of the materials for the top plate 240 but also by the configuration of the multiple cantilever-like springs, including the spring strength of individual cantilevers and the cantilever distribution density profile across the area of the cMUT element.

In principle, a cMUT element of the present invention may have an active area significantly larger than what would be possible with the conventional cMUT structures. The active area of a cMUT may be defined as the total movable area. For cMUT elements of a comparable overall size (cMUT element area), the active area of the cMUT element of the present invention may still be much greater than the total active area of the multiple cMUT cells in a conventional cMUT element. For example, the active area of the inventive cMUT can be close to 100% of the element (device) area, while the total active area of multiple cMUT cells in a conventional cMUT element may cover about 60-90% of the element (device) area at best. Usually, the higher the operation frequency is, the lower the active area percentage is for a conventional cMUT. In addition, even for a given movable area, the cMUT of the present invention potential yields a greater effective active area, which may be defined as the area of the effective electric field activating the capacitors.

The entire top plate 240 formed above the substrate wafer 201 may be movable without any clamped or fastened area. If desired, multiple cMUT elements can be formed by forming separation trenches through the top plate 240 and the spring layer 220. In principle, however, the entire cMUT structure with a very large active area may be used as a single cMUT element.

Furthermore, with the cMUT structure design in FIG. 2 the top plate 240 may be separated into a plurality of smaller top plates of identical or different sizes and shapes. Each smaller top plate may be addressed as a single addressable cMUT element; alternatively multiple smaller top plates may be combined together and addressed as a single cMUT element.

Furthermore, unlike the flexible membrane clamped on its edges (or posts) in the conventional cMUTs, the top plate 240 shown in FIG. 2 can be designed to be either flexible or rigid. With a rigid top plate, the whole surface of the cMUT, which may include any number of separate smaller top plates 240, may be movable with a very uniform displacement profile.

The location of the top electrode 250 may be at any position above the transducing space 265 defined between the top plate 240 and the upper portion 212 of the base. In a transmitter mode, the top plate 240 is actuated by the applied an electric field between two electrodes 250 and 260 to transmit the ultrasound into the medium. In a receiver mold, ultrasound is detected if it impinges on the top plate 240 cause the capacitance between two electrodes 250 and 260 to change.

Regardless of the configurations of the spring layer 220, it is envisioned that in some preferred embodiments, the cantilever-forming anchors (the lower portion 210 of the base) and the associated cantilever areas of cMUT element 200 together cover at least half of the device element area in order to achieve an effectively distributed cantilever-support of the top plate 240 and greater active areas. The cantilever areas may be defined as the total area of the cavities 225, or alternatively as the total area of the spring layer 220 covering the cavities. Preferably the cantilever-forming anchor areas and the cantilever areas are at least 80% of the device element area, and further preferably near 100% of the device element area. Base areas that only support an electrode but do not serve to anchor a cantilever are not required, and preferably not formed at all within the transducer element area of the substrate wafer 201 in order to maximize the cantilever-forming anchor areas as described above.

Within the general principle of the present invention, there is great room of design freedom in terms of the overall size of each addressable device element, the size, shape and arrangement of the cavities, the size, shape and arrangement of the anchors for cantilevers, the size, shape and arrangement of the connectors, and the thickness, shape, segment (separation) pattern and material selection of each layers (the substrate wafer, the spring layer and the top plate layer).

A cMUT element in accordance with the present invention is no longer necessarily made of multiple cells each having a flexible membrane. Instead, the cMUT element may have a single (rigid or flexible) top plate. Even if multiple top plates are used, these top plates do not need to be clamped at some cell boundaries like the membranes for each cell in the prior art. The multiple top plates further do not need to be identical to each other. Generally, even with multiple top plates, only a small number of the top plates would be necessary for each addressable device element, much fewer than the number of individually clamped cells that would have been required in conventional cMUT designs.

The cantilevers formed from the spring layer function as embedded springs that can be of a variety of spring strength, size and density variations. These embedded springs may be made of a single contiguous flexible membrane or multiple flexible membranes of identical or different size and shape. The locations of the spring-plate connectors (e.g., connectors 230) may be designed to obtain the optimal displacement for the top plate or the desired frequency response for the cMUT during the cMUT operation. The configuration of the top plate 240, such as using smaller top plate segments, may also be adjusted to achieve desired frequency response for a CMUT element with a relative large size.

In summary, unlike the cMUTs in the prior art, there may be no clamped (or fixed) area on the transducer surface of this invention, and the top surface of the cMUT may be made of a single top plate or multiple top plates which are supported by springs (cantilevers) deployed at strategic locations. As a result the cMUT in accordance with the present invention has the potential to solve many problems of the prior cMUTs mentioned in the background section. The potential advantages may include:

(1) Since the entire top surface of the transducer is movable with a much more uniform displacement, both the average displacement and the average electrical field between two electrodes of the cMUT element may be improved. This may lead to better transmission and reception performances.

(2) With the design of the present invention, it is possible to make a transducer with no or very little inactive surface area so that the device fill factor can be near perfect. This is especially important for a high frequency cMUT because the transducer dimension is small.

(3) The parasitic capacitance of the transducer can be dramatically decreased by selecting proper properties of the embedded springs. For example, non-conductive materials may be used for the spring layer. This improves the transducer sensitivity.

(4) The transducer breakdown voltage can be improved by using a proper material for the spring layer so that a high electrical field may be obtained between two electrodes to improve the device performance.

(5) The uniformity of the cMUT surface displacement can be further improved by increasing the stiffness of the top plate. With a properly chosen thickness of the top plate, the cMUT surface displacement may have minimum impact or no impact on ultrasonic beam pattern emitted from the transducer surface.

(6) Because the cMUT cell boundary pattern within the cMUT element surfaces can be eliminated with the new design, there is no high frequency limitation caused by such cell boundary patterns. This may improve the bandwidth of the cMUT.

(7) Without having to use a great number of individual cells in each cMUT element, the phase difference of the motion at the different locations (different cells) on the cMUT surface is minimized. This is true especially if a rigid top plate is used. This can improve the device performance, especially when the cMUT works in a high quality factor (Q-factor) condition, e.g., in air or low pressure environment.

(8) The anchors (sidewall anchors 203 for anchoring the spring layer 220) of the cMUT may be made slightly smaller than the top plate so that there is more room at the cMUT element edge for adding decoupling structures between the cMUT elements to reduce the cross coupling.

(9) The present invention provides more design flexibility for the MUTs than those of the prior arts. For example, the top plate 240 may be designed to be of different shapes and configurations; the embedded springs may have different shapes and different spring constants by selecting the proper materials and dimensions. Moreover, the embedded springs can attach to the different locations on the top plate 240.

The cantilever-like spring structures shown in FIG. 2 may be replaced by other types of flexible structures that may effectively function as a spring with proper support to the top plate (240). In addition to the spring structures described in the several patent applications referenced to and incorporated herein, additional flexible structures are described below.

Figure 3:
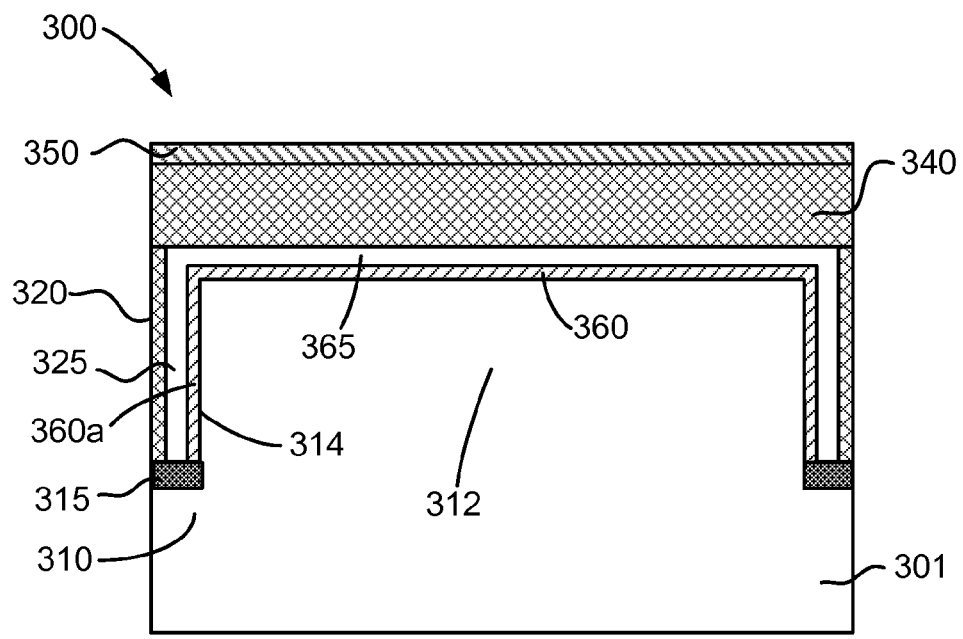
FIG. 3 shows a basic unit of a second embodiment of an embedded-spring cMUT in accordance with the present invention.

FIG. 3 shows a second embodiment of an embedded-spring cMUT in accordance with the present invention. FIG. 3 is an enlarged view of a selected portion 300 of an embedded spring micro-electro-mechanical transducer (ESMUT). The ESMUT portion 300 is a part of a complete ESMUT element (not shown). Two springs are shown in order to give structural context.

The ESMUT portion 300 is built on a substrate 301, on which is a base including a lower base portion 310 and an upper base portion 312. A top plate 340 is disposed above the upper base portion 312 forming a gap 365 therebetween. A spring-like structure having a vertical bendable connector 320 connecting the top plate 340 and the lower portion 310 of the base through a spring anchor 315. The optional spring anchor 315 is added to insulate the vertical bendable connector 320 from the substrate 301 if needed.

In operation, bending of the vertical bendable connector 320 causes a vertical displacement of the top plate 340. As the top plate 340 is connected by multiple bendable connectors 320 similar to each other, bending of the bendable connectors 320 may result in a vertical translation movement by the top plate 340. In some embodiments, the top plate 340 is desirably a rigid plate (being significantly more rigid than the spring layer 320), and thus can be transported in a piston like fashion.

In a cMUT configuration, the top plate 340 further has a top electrode 350 as one of its transducer members. Correspondingly, the top of the upper portion 312 of the base has a bottom electrode 360, which may either be a separate layer disposed on rest of the upper portion 312, or an integral part of the upper portion 312 if the upper portion 312 is made of a conductive material.

The upper portion 312 of the base may be a separate layer disposed on the lower portion 310. Alternatively, both the upper portion 312 and the lower portion 310 may constitute an integral base, which itself may either be a separate layer placed on the substrate 301, or an integral part thereof. In simplest embodiments, the upper portion 312 may be a layer having a pattern of trench openings 325 from a top side of the upper portion 312 to the lower portion of the base. The trench openings 325 may either be separate narrow openings or extended trenches extending across the surface area of the upper portion 312. A plurality of vertical bendable connectors 320 is disposed in the pattern of trench openings 325.

Figure 4:
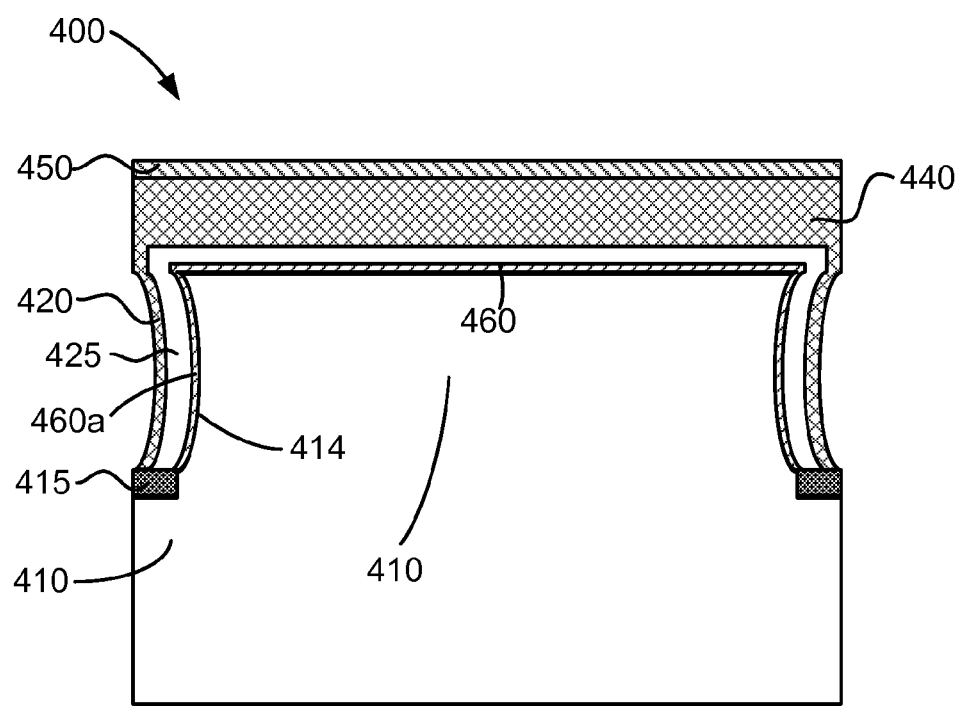
FIG. 4 shows a basic unit of a third embodiment of an embedded-spring cMUT in accordance with the present invention.

FIG. 4 shows a third embodiment of an embedded-spring cMUT in accordance with the present invention. FIG. 4 is an enlarged view of a selected portion 400 of an embedded spring micro-electro-mechanical transducer (ESMUT). The ESMUT portion 400 is a part of a complete ESMUT element (not shown). Two springs are shown in order to give structural context.

The ESMUT portion 400 is similar to the ESMUT portion 300 shown in FIG. 3. However, the ESMUT portion 400 is characterized by a spring-like structure having a curved bendable connector 420 connecting the top plate 440 and the lower portion 410 of the base. Compared to the straight vertical bendable connector 320, the curved bendable connector 420 may be easier to bend and have more controllable and more consistent bending behavior. A spring anchor 415 similar to the spring anchor 315 in FIG. 3 is also used for further insulation.

In a cMUT configuration, the top plate 440 further has a top electrode 450 as one of its transducer members. Correspondingly, the top of the upper portion 412 of the base has a bottom electrode 460, which may either be a separate layer disposed on rest of the upper portion 412, or an integral part of the upper portion 412 if the upper portion 412 is made of a conductive material.

In simplest embodiments, the upper portion 412 may be a layer having a pattern of trench openings 425 from a top side of the upper portion 412 to the lower portion of the base. A plurality of vertical bendable connectors 420 is disposed in the pattern of trench openings 425.

Furthermore, the bendable connector 320 or 420 may be made of a conductive material and serve as a part of the movable electrode (along with the top electrode 350 or 450). The extra electrode on the bendable connector 320 or 420 would form an extra capacitor with the extended bottom electrode 360a or 460a placed on the sidewall 314 or 414 of the upper portion 312 or 412 of the base. Like the primary bottom electrode 360 or 460, the extended bottom electrode 360a and 460a may either be a separate layer disposed on rest of the upper portion 312 or 412 of the base, or an integral part thereof if the upper portion 312 or 412 is made of a conductive material. As a result, the transducer in FIG. 3 and FIG. 4 may have a larger active area than other designs to attain a higher capacitance and thus achieve better transducer performance. The transducing space 325 or 425 of the extra capacitor is defined by the gap 325 or 425 between the bendable connectors (springs) 330 or 430 and the extended electrode 360a or 460a on the sidewall 314 or 414 of the upper portion 312 or 412.

Fabrication Methods:

The electrostatic transducer in accordance with the present invention may be fabricated using a variety of methods. The fundamental techniques and processes disclosed in the several patent applications referenced to and incorporated herein, especially International Application (PCT) No. PCT/IB2006/051567, entitled METHODS FOR FABRICATING MICRO-ELECTRO-MECHANICAL DEVICES, filed on May 18, 2006, may be used in any combination and adapted for fabricating the cMUT structures disclosed herein. Several examples of such adapted processes are described below.

FIGS. 5.1-5.11 show a fabrication process for making a cMUT of the present invention using wafer bonding process. The steps of the process are described below.

In step one (FIG. 5.1), a desired recess pattern is formed on substrate 501.

In step two (FIG. 5.2), the substrate 501 is further patterned to a desired thickness pattern to define anchors 510 and posts 515. The anchors 510 will become a part of the lower portion of the base to support the spring layer to be formed. The optional posts 515 will serve as motion stoppers.

In step three (FIG. 5.3), An SOI wafer including the desired spring layer 520 is bounded on the substrate 501. The handle wafer and the box of the SOI wafer are subsequently removed to form the spring layer 520. Alternatively, a prime wafer may be used to introduce the spring layer 520.

In step four (FIG. 5.4), the spring layer 520 is patterned in preparation for forming or connecting the spring-played connectors and the upper portion of the base in the next steps.

In step five (FIG. 5.5), a prime layer 560 is bonded to the spring layer 520, and is ground and polished to a desired thickness to form the upper portion (560) of the cMUT base. Alternatively, an SOI wafer may used at this step to replace the prime wafer. A separate conductive layer may be deposited to form a bottom electrode in this step if needed.

In step six (FIG. 5.6), a dielectric layer 562 is deposited and patterned to partially form the spring-plate connectors to support the top plate to be introduced.

In step seven (FIG. 5.7), an insulation layer 564 is grown and patterned. The optional insulation layer 564 becomes the top of the upper portion of the cMUT base. The dielectric layer 562 and the insulation layer 564 have different heights, with the former being taller to support the top plate to be introduced and to define a gap between the top plate and the insulation layer 564.

In step eight (FIG. 5.8), the layer 560 is patterned to form the upper portions 560. Trench openings are formed through the layer 560. This also forms the spring-plate connectors 530 passing through the trench openings.

In step nine (FIG. 5.9), a prime wafer 540 is bonded over the spring-plate connectors 530, and ground and polished to form a top plate (540). Alternatively, an SOI wafer may be used in this step to replace the prime wafer.

In step ten (FIG. 5.10), a metal layer 550 is deposited and patterned to form the top electrode.

In step eleven (FIG. 5.11), trenches 555 are etched between the cMUT evidence to separate the individual cMUT elements.

FIGS. 6.1-6.10 show a fabrication process for making a cMUT of the present invention using sacrificial technology. The steps of the process are described below.

In step one (FIG. 6.1), a first sacrificial layer 681 is deposited and patterned on substrate 601.

In step two (FIG. 6.2), a material layer is deposited and patterned to form both the spring layer 620 and a part of the lower portion 610 of the cMUT base to support the spring layer 620. Vias 621 for sacrificial layer removal are also formed through the spring layer 620. Although in the cross-sectional view the spring layer 620 may appear to be disconnected from the lower portion 610 of the cMUT base, in 2-D or 3-D view these components are connected to form the cantilever-like spring structures of the present invention.

In step three (FIG. 6.3), a second sacrificial layer 682 is deposited and patterned. The second sacrificial layer 682 and the first sacrificial layer may be designed to conduct to each other in order to facilitate easier sacrificial removal.

In step four (FIG. 6.4), layer 660 is deposited to form the upper portion of the cMUT base. If the layer 660 is made of the conductive material, this also forms the bottom electrode. Ultimately, a separate conductive layer may be deposited to form a bottom electrode in this step.

In step five (FIG. 6.5), a third sacrificial layer 683 is deposited and patterned to partially define the suppression gap between the bottom electrode and the top electrode to be formed.

In step six (FIG. 6.6), a thin-film layer 641 is deposited to form a part of the top plate 640 (to be completed) of the cMUT. Vias (not shown) may also be formed in this step to access the sacrificial layers.

In step seven (FIG. 6.7), sacrificial materials (681, 682 and 683) are removed. The vias may be sealed subsequently by spinning or depositing another thin-film layer.

In step eight (FIG. 6.8), a thin conductive layer 650 is deposited over the thin-film layer 641 to form the top electrode.

In step nine (FIG. 6.9), a material layer 642 is deposited to a desired thickness to complete the top plate 640 of the cMUT. In this particular embodiment, the top plate 640 comprises the thin-film layer 640, the thing conductive layer 650 and the material layer 642. This is an example where the top electrode (650) is embedded within the top plate (640). Other type of configurations, including using a conductive material for the entire top plate or depositing the conductive layer on top of the top plate, may also be used.

In step ten (FIG. 6.10), trenches 655 are etched between the cMUT evidence to separate the individual cMUT elements.

FIGS. 7.1-7.7 show a fabrication process for making another cMUT of the present invention. The steps of the process are described below.

In step one (FIG. 7.1), a first thermal oxide layer 702 is grown and patterned on substrate 701.

In step two (FIG. 7.2), a second thermal oxide layer 722 is deposited and patterned to form an insulation layer. At the same time, the first thermal oxide layer 702 is patterned to form a part of the vertical spring 720.

In step three (FIG. 7.3), the substrate 701 is etched to form deep trenches 725 and a complete vertical springs 720 therein.

In step four (FIG. 7.4), a prime wafer 740 is bonded over the vertical springs 720 to form the top plate 740.

In step five (FIG. 7.5), a metal layer 750 is deposited and patterned to form the top electrode.

In step six (FIG. 7.6), trenches 755 are etched between the cMUT evidence to separate the individual cMUT elements.

The micro-electro-mechanical transducer in accordance with the present invention has been described in detail along with the figures and exemplary embodiments. The design of the micro-electro-mechanical transducer of the present invention is particularly suitable for applications in capacitive micromachined ultrasonic transducers (cMUT), but can also be used in other micro-electro-mechanical devices which have a movable mechanical part to transform energy.

In particular, the micro-electro-mechanical transducer in accordance with the present invention may be fabricated using the fabrication methods or incorporated in the micro-electro-mechanical transducer as disclosed in international patent applications (PCT) No. PCT/IB2006/051566, entitled THROUGH-WAFER INTERCONNECTION, filed on May 18, 2006; No. PCT/IB2006/051567, entitled METHODS FOR FABRICATING MICRO-ELECTRO-MECHANICAL DEVICES, filed on May 18, 2006; No. PCT/IB2006/051568, entitled MICRO-ELECTRO-MECHANICAL TRANSDUCERS, filed on May 18, 2006; No. PCT/IB2006/051569, entitled MICRO-ELECTRO-MECHANICAL TRANSDUCERS, filed on May 18, 2006; and No. PCT/IB2006/051948, entitled MICRO-ELECTRO-MECHANICAL TRANSDUCER HAVING AN INSULATION EXTENSION, filed on Jun. 16, 2006. These patent applications are hereby incorporated herein by reference.

In the foregoing specification, the present disclosure is described with reference to specific embodiments thereof, but those skilled in the art will recognize that the present disclosure is not limited thereto. Various features and aspects of the above-described disclosure may be used individually or jointly. Further, the present disclosure can be utilized in any number of environments and applications beyond those described herein without departing from the broader spirit and scope of the specification. We claim all such modifications and variations that fall within the scope and spirit of the claims below. The specification and drawings are, accordingly, to be regarded as illustrative rather than restrictive. It will be recognized that the terms "comprising," "including," and "having," as used herein, are specifically intended to be read as open-ended terms of art.

The invention claimed is:

1. A micro-electro-mechanical transducer comprising:
   a base having a lower portion and an upper portion;
   a top plate disposed above the upper portion of the base forming a gap therebetween;
   a spring-like structure disposed between the top plate and the lower portion of the base, the spring-like structure having a spring layer connected to the lower portion of the base and a spring-plate connector connecting the spring layer and the top plate; and
   a first transducing member on the top plate and a second transducing member included in the base or carried by the base.

2. The micro-electro-mechanical transducer of claim 1 wherein the first transducing member is an electrode.

3. The micro-electro-mechanical transducer of claim 1 wherein the second transducing number comprises a conductive layer included in the upper portion of the base and serving as an electrode.

4. The micro-electro-mechanical transducer of claim 3 wherein the conductive layer is a separate layer disposed on rest of the upper portion.

5. The micro-electro-mechanical transducer of claim 1 further comprising a motion stopper disposed under the spring layer to limit a maximum vertical displacement thereof.

6. A micro-electro-mechanical transducer comprising:
   a first support layer supporting a first electrode;
   a second support layer supporting a second electrode, the second support layer having a pattern of openings and being connected to a substrate through a plurality of anchors;
   a spring layer below the second support layer, the spring layer being connected to the plurality of anchors at various locations; and
   a plurality of vertical connectors passing through the pattern of openings on the second support layer to connect the first support layer and the spring layer.

7. The micro-electro-mechanical transducer of claim 6 wherein the plurality of anchors each have a sidewall receding from an edge of a nearby opening of the second support layer to define a cavity under the second support layer, and wherein the spring layer forms a plurality of cantilevers each anchored at the respective sidewall of the plurality of anchors.

8. The micro-electro-mechanical transducer of claim 6 further comprising a motion stopper disposed under the spring layer to limit a maximum vertical displacement thereof.

9. A micro-electro-mechanical transducer comprising:
a base having a lower portion and an upper portion;
a top plate disposed above the upper portion of the base forming a gap therebetween;
a spring-like structure disposed between the top plate and the lower portion of the base, the spring-like structure having a vertical bendable connector connecting the top plate and the lower portion of the base; and
a first transducing member on the top plate and a second transducing member included in the base or carried by the base.

10. The micro-electro-mechanical transducer of claim 9 wherein the transducing member is an electrode.

11. The micro-electro-mechanical transducer of claim 9 wherein the upper portion of the base comprises an electrode serving as the second transducing member.

12. The micro-electro-mechanical transducer of claim 9 wherein the vertical bendable connector has a curved shape.

13. A micro-electro-mechanical transducer comprising:
a base having a lower portion and an upper portion;
a top plate disposed above the upper portion of the base forming a gap therebetween;
a spring-like structure disposed between the top plate and the lower portion of the base, the spring-like structure having a spring layer connected to the lower portion of the base and a spring-plate connector connecting the spring layer and the top plate; and
a transducing member on the top plate,
wherein the lower portion of the base has a sidewall receding from an edge of the upper portion of the base to define a cavity under the upper portion, the spring layer being connected to the sidewall of the lower portion to form a cantilever disposed in the cavity.

14. A micro-electro-mechanical transducer comprising:
a base having a lower portion and an upper portion;
a top plate disposed above the upper portion of the base forming a gap therebetween;
a spring-like structure disposed between the top plate and the lower portion of the base, the spring-like structure having a vertical bendable connector connecting the top plate and the lower portion of the base; and
a transducing member on the top plate,
wherein the upper portion of the base comprises a layer material having a pattern of trench openings passing from a top to the lower portion of the base, wherein the spring-like structure comprises a plurality of vertical bendable connectors disposed in the pattern of trench openings.

15. A micro-electro-mechanical transducer comprising:
a base having a lower portion and an upper portion;
a top plate disposed above the upper portion of the base forming a gap therebetween;
a spring-like structure disposed between the top plate and the lower portion of the base, the spring-like structure having a vertical bendable connector connecting the top plate and the lower portion of the base; and
a transducing member on the top plate,
wherein the vertical bendable connector connects to the lower portion of the base through an anchor layer.

16. A micro-electro-mechanical transducer comprising:
a base having a lower portion and an upper portion;
a top plate disposed above the upper portion of the base forming a gap therebetween;
a spring-like structure disposed between the top plate and the lower portion of the base, the spring-like structure having a vertical bendable connector connecting the top plate and the lower portion of the base; and
a transducing member on the top plate,
wherein the vertical bendable connector includes a first vertical electrode, and the upper portion of the base has a sidewall including a second vertical electrode, the first electrode and the second electrode forming a vertical capacitor.

* * * * *